United States Patent
Kong et al.

(10) Patent No.: US 12,353,693 B2
(45) Date of Patent: Jul. 8, 2025

(54) MEDICAL TREATMENT SYSTEM USING TRANSPARENT DISPLAY MODULE

(71) Applicant: SEOUL NATIONAL UNIVERSITY HOSPITAL, Seoul (KR)

(72) Inventors: Hyoun Joong Kong, Seoul (KR); Kyu Eun Lee, Seoul (KR)

(73) Assignee: SEOUL NATIONAL UNIVERSITY HOSPITAL, Seoul (KR)

( * ) Notice: Subject to any disclaimer, the term of this patent is extended or adjusted under 35 U.S.C. 154(b) by 209 days.

(21) Appl. No.: 18/272,599

(22) PCT Filed: Dec. 30, 2021

(86) PCT No.: PCT/KR2021/020245
§ 371 (c)(1),
(2) Date: Oct. 2, 2023

(87) PCT Pub. No.: WO2022/158746
PCT Pub. Date: Jul. 28, 2022

(65) Prior Publication Data
US 2024/0077996 A1    Mar. 7, 2024

(30) Foreign Application Priority Data

Jan. 20, 2021 (KR) .................. 10-2021-0008309
Dec. 29, 2021 (KR) .................. 10-2021-0191542

(51) Int. Cl.
*G06F 3/048* (2013.01)
*G06F 3/01* (2006.01)
(Continued)

(52) U.S. Cl.
CPC .......... *G06F 3/04845* (2013.01); *G06F 3/013* (2013.01); *G16H 80/00* (2018.01)

(58) Field of Classification Search
CPC ...... G06F 3/04845; G06F 3/013; G16H 80/00
See application file for complete search history.

(56) References Cited

U.S. PATENT DOCUMENTS 10,136,742 B1 * 11/2018 Leslie .................. G06F 3/0482
10,269,453 B2    4/2019 Lee et al.
(Continued)

FOREIGN PATENT DOCUMENTS

JP    2013-041411 A    2/2013
KR   10-2014-0144992 A   12/2014
(Continued)

OTHER PUBLICATIONS

Hirakawa et al., A Collaborative Augmented Reality System using Transparent Display, 2004, IEEE, 7 pages (Year: 2004).*
(Continued)

*Primary Examiner* — Linh K Pham
(74) *Attorney, Agent, or Firm* — Revolution IP, PLLC (57) ABSTRACT

A medical treatment system includes a transparent display located between a patient and a medical staff and configured to display, a plurality of interface, first and second gaze trackers respectively mounted on both sides of the transparent display to detect pupils of the medical staff and patient and configured to acquire positional coordinates of the pupils of the medical staff and patient in a three-dimensional space, a region setting unit configured to set a gaze exchange region based on an intersection point where a virtual connection line between the positional coordinates of the pupils of the medical staff and patient intersects a plane of the transparent display, and a control unit configured to rearrange the plurality of interface windows by moving at least one interface window overlapping the gaze exchange region outside the gaze exchange region.

8 Claims, 4 Drawing Sheets

(51) Int. Cl.
*G06F 3/04845* (2022.01)
*G16H 80/00* (2018.01)

(56) References Cited

U.S. PATENT DOCUMENTS

| | | | |
|---|---|---|---|
| 2014/0306900 A1* | 10/2014 | Son | G06F 3/0484 |
| | | | 345/173 |
| 2014/0368442 A1* | 12/2014 | Vahtola | G06F 3/013 |
| | | | 345/173 |
| 2015/0235346 A1 | 8/2015 | Kim et al. | |
| 2015/0332091 A1* | 11/2015 | Kim | H04N 5/2621 |
| | | | 382/103 |
| 2017/0060512 A1* | 3/2017 | Rakshit | G06F 3/041 |
| 2017/0090266 A1* | 3/2017 | Wang | H10K 50/846 |
| 2017/0153379 A1* | 6/2017 | Chang | G02B 6/0081 |
| 2017/0235360 A1* | 8/2017 | George-Svahn | G02B 27/017 |
| | | | 345/173 |
| 2018/0033171 A1* | 2/2018 | Rakshit | G06V 20/00 |
| 2020/0372902 A1* | 11/2020 | Takami | G03B 21/62 |

FOREIGN PATENT DOCUMENTS

| | | |
|---|---|---|
| KR | 10-2015-0090735 A | 8/2015 |
| KR | 10-2015-0096826 A | 8/2015 |
| KR | 10-1679265 B1 | 11/2016 |
| KR | 10-1691564 B1 | 12/2016 |

OTHER PUBLICATIONS

Edelmann et al., FACE2FACE—A System for Multi-Touch Collaboration With Telepresence, 2012, IEEE, 4 pages (Year: 2012).*

He et al., CollaboVR: A Reconfigurable Framework for Creative Collaboration in Virtual Reality, 2020, IEEE, 13 pages. (Year: 2020).*

Ishii et al., ClearBoard: A Seamless Medium for Shared Drawing and Conversation with Eye Contact, 1992, ACM, 10 pages, (Year: 1992).*

International Search Report for PCT/KR2021/020245 mailed Apr. 11, 2022 from Korean Intellectual Property Office.

* cited by examiner

MEDICAL TREATMENT SYSTEM USING TRANSPARENT DISPLAY MODULE

TECHNICAL FIELD

The present invention relates to a medical treatment system using a transparent display module, and more particularly, to a medical treatment system using a transparent display module in which gaze exchange and information exchange between a doctor and a patient may be simultaneously performed.

BACKGROUND ART

Recently, the PC environment-based health checkup has been rapidly expanded in a face-to-face service situation between a doctor and a patient, and accordingly, use of a diagnosis technique in which the doctor faces the patient is shrunk, and gaze exchange between the doctor and the patient is blocked.

The gaze blocking between the doctor and the patient reduces communion with the partner, causing a decrease in satisfaction of the service. The decrease in satisfaction leads to a decrease in profit of a service provider and a decrease in customers. The known treatment method reduces rapport and satisfaction, which is a deep trust between a doctor and a patient based on non-verbal communication.

Most hospitals computerize data and check patient information with electronic charts. A doctor's gaze is usually fixed onto a computer because all diagnoses and actions of the doctor have to be recorded on charts.

In general, when a monitor for providing information is used separately to obtain gaze with a patient and provide information, it tends to take additional treatment time, and since a doctor and the patient stare at the monitor during treatment, there is a limit that the doctor and the patient are hard to actually exchange gaze with each other.

When a doctor diagnoses long a patient while observing and touching the patient, more accurate diagnosis may be made, and unnecessary examination and treatment may be reduced. In addition, treatment results may be improved when rapport, which is a deep trust formed between a patient and a doctor through gaze exchange, is deeply formed.

Therefore, there is a need for a new type of medical interface in which various information exchanges and gaze exchanges may be performed simultaneously during a medical treatment process between a doctor and a patient.

The background technology of the present invention is disclosed in Korean Patent Publication No. 2015-0090735 (published on Aug. 6, 2015).

DISCLOSURE

Technical Problem

An object of the present invention is to provide a medical treatment system using a transparent display module capable of increasing patient satisfaction and treatment efficiency by simultaneously enabling gaze exchange and information exchange between a doctor and a patient.

Technical Solution

The present invention provides a medical treatment system, which uses a transparent display module, including a transparent display located between a patient and a medical staff and configured to display, on a screen, a plurality of interface windows for providing a plurality of electronic medical charts related to the patient, first and second gaze trackers respectively mounted on both sides of the transparent display to detect pupils of the medical staff and patient and provide gaze tracking information and configured to acquire positional coordinates of the pupils of the medical staff and patient in a three-dimensional space, a region setting unit configured to set a gaze exchange region based on an intersection point where a virtual connection line between the positional coordinates of the pupils of the medical staff and patient intersects a plane of the transparent display, and a control unit configured to rearrange the plurality of interface windows by moving at least one interface window overlapping the gaze exchange region outside the gaze exchange region.

In addition, the transparent display may be implemented as a single-sided display, and the control unit may display the plurality of interface windows on one side of the transparent display viewed by the medical staff.

In addition, the transparent display may be implemented as a double-sided display, and the control unit may display the plurality of interface windows on both sides of the transparent display so as to correspond to each other and displays the plurality of interface windows in parallel on the same position on both sides.

In addition, the region setting unit may set a region of a set radius based on the intersection point or a region of a preset size and shape around the intersection point as the gaze exchange region.

In addition, the control unit may arrange the plurality of interface windows on the screen of the transparent display in tiers so as to overlap each other and may display an interface window with a highest priority at a top portion based on a preset order or importance.

In addition, when a screen gaze point of the medical staff identified based on gaze tracking information of the first gaze tracker for tracking gaze of the medical staff is maintained for a set time or more, the control unit may move a target interface window at a position corresponding to the screen gaze point to the top portion.

In addition, the control unit may display the plurality of interface windows on the both sides of the transparent display so as to correspond to each other, and when the screen gaze point is maintained for the set time, the control unit may simultaneously move all target interface windows on both sides of a position corresponding to the screen gaze point to a top portion of a corresponding surface.

In addition, the medical treatment system may further include a motion sensor configured to detect entry of the patient into a treatment room, wherein, when the entry of the patient is detected through the motion sensor, the control unit may switch operations of the first and second gaze trackers to an active state to start an operation of tracking the pupils of the medical staff and patient.

Advantageous Effects

According to the present invention, gaze exchange and information transfer between a doctor and a patient are simultaneously performed based on a transparent display, and accordingly, patient satisfaction and treatment efficiency may be increased, and the quality of medical care may be increased.

According to the present invention, a gaze intersection point between a patient and a doctor facing a transparent display is recognized, and based on this, medical software interfaces existing on a screen of the transparent display are automatically redisposed to an outer periphery therefrom, and accordingly, there are effects that charts may be checked without obstruction of gaze between the doctor and patient, and gaze exchange and interaction between the doctor and patient may be continued during treatment.

BEST MODE

Then, embodiments of the present invention will be described in detail with reference to the accompanying drawings such that those skilled in the art to which the present invention belongs may easily practice the embodiments. However, the present invention may be implemented in many different forms and is not limited to the embodiments described herein. In addition, in order to clearly describe the present invention in the drawings, parts irrelevant to the description are omitted, and similar reference numerals are attached to similar parts throughout the specification.

Throughout the specification, when a portion or a unit is described to be "connected" to another portion or another unit, this includes not only a case of being "directly connected", but also a case of being "electrically connected" with other elements therebetween. In addition, "including" a certain component means that other components may be further included, rather than excluding other components unless otherwise stated.

Figure 1:
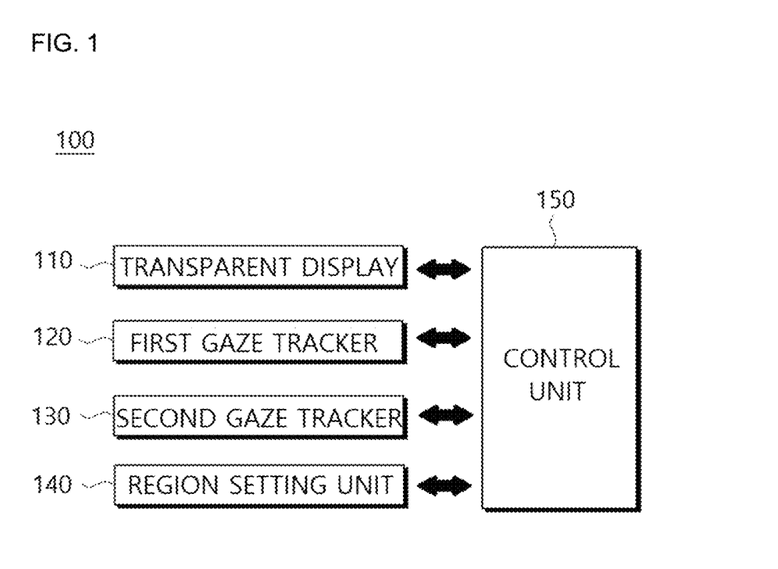
FIG. 1 is a diagram illustrating a configuration of a medical treatment system using a transparent display module, according to an embodiment of the present invention.
Figure 2:
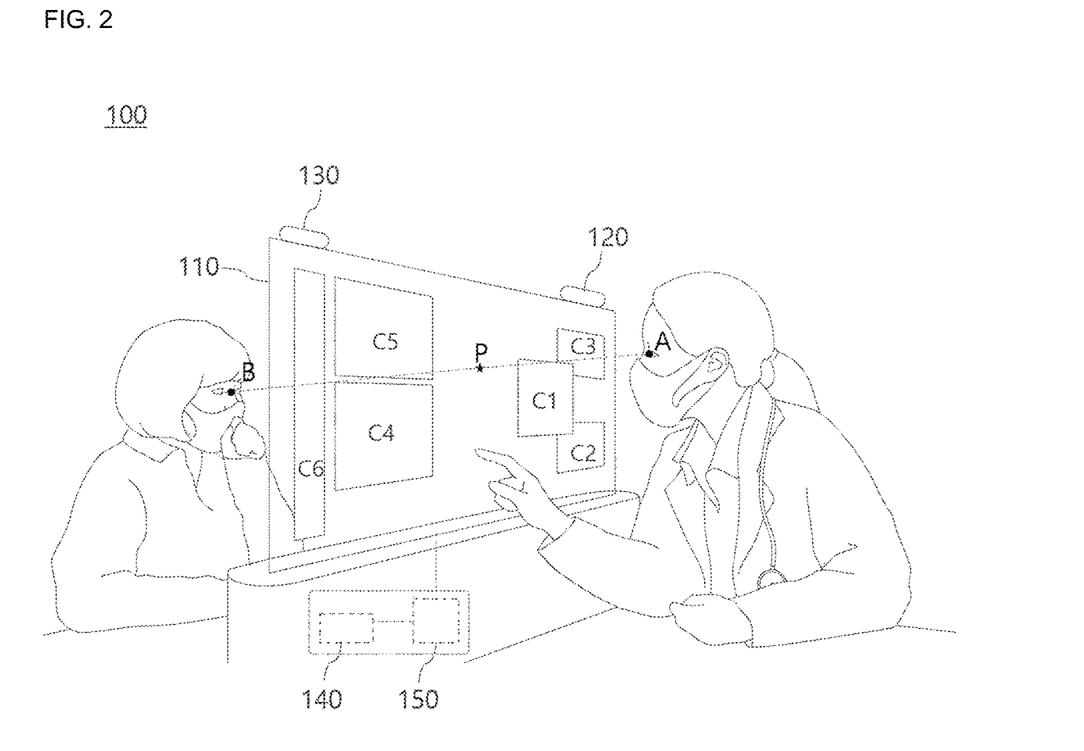
FIG. 2 is a view illustrating an implementation of the medical treatment system illustrated in FIG. 1.

FIG. 1 is a diagram illustrating a configuration of a medical treatment system using a transparent display module, according to an embodiment of the present invention, and FIG. 2 is a view illustrating an implementation of the medical treatment system illustrated in FIG. 1.

As illustrated in FIGS. 1 and 2, a medical treatment system 100 using a transparent display module, according to an embodiment of the present invention, includes a transparent display 110, first and second gaze trackers 120 and 130, a region setting unit 140, and a control unit 150. Here, operations of the respective units 110 to 140 and data flow between the respective units may be controlled by the control unit 150.

As illustrated in FIG. 2, the transparent display 110 is located between a patient and a medical staff, and displays, on the screen, a plurality of interface windows C (C1 to C7) for providing a plurality of electronic medical charts related to the patient.

The electronic medical charts displayed on the respective interface windows may correspond to various types of data, including text, images, diagrams, and so on, and include data on various medical records and clinical information related to patients, images of radiology examination results (for example, CT, MRI, X-ray, ultrasound images), images of affected areas, and so on.

In the transparent display 110, a screen configuration, display information, and so on may be manipulated by using at least one method of input means, such as a mouse or keyboard, screen touch, and user gaze detection.

In addition, the transparent display 110 may operate in conjunction with a user terminal, such as a PC, a desktop computer, a notebook computer, a tablet PC, or a pad. In addition, the transparent display 110 may be implemented to have such a computing function built in, and in this case, may be configured to include a memory, an input/output (I/O) interface, and a communication unit.

The transparent display 110 may be directly connected to a hospital server through a network or may be connected through a user terminal to search, inquire, and provide various types of medical chart information related to patients. In addition, the transparent display 110 may be implemented in a double-sided type or a single-sided type.

The first and second gaze trackers 120 and 130 are respectively mounted on both sides of the transparent display 110 to detect eyes of a medical staff and a patient by using built-in cameras, and provide gaze tracking information. In addition, the first and second gaze trackers 120 and 130 respectively acquire positional coordinate values of the pupils of a medical staff and a patient in a three-dimensional space.

The first gaze tracker 120 is installed in front of the transparent display 110 to recognize and detect pupils of a medical staff, and obtains three-dimensional coordinate values (for example, x1, y1, and z1) of a pupil position A of a medical staff. The second gaze tracker 130 is installed on the back of the transparent display 110 to recognize and detect pupils of a patient, and obtains three-dimensional coordinate values (for example, x2, y2, and z2) of a pupil position B of a patient.

The first and second gaze trackers 120 and 130 may be implemented in the form of an eye tracker. Each of the gaze trackers 120 and 130 may be integrally configured with the transparent display 110 or may be mounted separately on the outside of the transparent display 110. In addition, each of the gaze trackers 120 and 130 may be connected to the control unit 150 wired or wirelessly while being installed on the transparent display 110.

The first and second gaze trackers 120 and 130 may transmit pupil positions, gaze tracking information, and so on detected from a user to the control unit 150. The control unit 150 may provide information received from each of the gaze trackers 120 and 130 to the region setting unit 140 and generate a signal for manipulating a screen of the transparent display 110 by using gaze tracking information of a user.

Here, the first and second gaze trackers 120 and 130 may know their three-dimensional positions in advance based on a flat position of the transparent display or a preset three-dimensional reference point, or may calculate and acquire the three-dimensional positions through calibration or so on, and may obtain actual three-dimensional coordinate values of pupils by using their own three-dimensional coordinates, pixel sizes of the pupils on a captured image, positional coordinates of the pupils of an image, and so on. Of course, a coordinate calibration process of each of the gaze trackers 120 and 130 may be performed based on the position of the transparent display 110. There may be more various embodiments for pupil position detection using such eye trackers.

As illustrated in FIG. 2, the region setting unit 140 obtains an intersection point P where a virtual connection line (A-B connection line) connecting positional coordinates of each pupil of a medical staff and a patient meets a plane of the transparent display 110, and virtually sets, on the display plane, a gaze exchange region that enables interaction between the medical staff and the patient based on the intersection point P.

The region setting unit 140 may set a set distance region or a region of a set radius on the left and right of the intersection point P as the gaze exchange region, and in addition, may set the gaze exchange region having a preset size and shape around the intersection point P. The region setting unit 140 provides information on the set gaze exchange region to the control unit 150.

The control unit 150 moves and rearranges at least one interface window overlapping the gaze exchange region among a plurality of interface windows provided on the transparent display 110 outside the gaze exchange region, and obtains a gaze exchange space between a patient and a medical staff therethrough.

Figure 3:
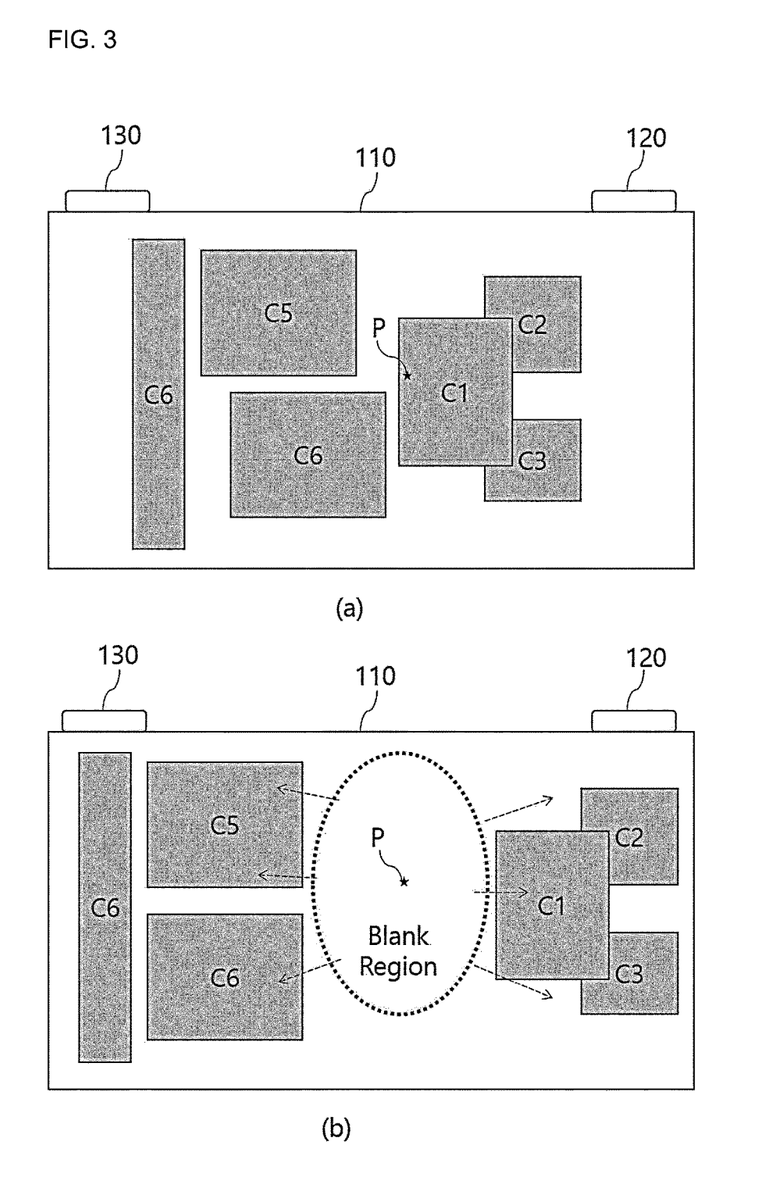
FIG. 3 illustrates states in which interface windows are rearranged by being moved to an outer periphery based on a gaze exchange point according to an embodiment of the present invention.

FIG. 3 illustrates a state in which interface windows are rearranged by moving them to the outer periphery based on the gaze exchange point according to an embodiment of the present invention.

(a) of FIG. 3 illustrates an example of a screen of the transparent display 110 before a gaze exchange point between a patient and a medical staff is detected, and (b) thereof illustrates a state in which a gaze exchange region (blank region) of a set size for exchanging gaze is obtained according to detection of the gaze exchange point and interface windows are rearranged in an outer periphery of the gaze exchange region.

In this case, the gaze exchange region corresponds to a blank region that is empty such that gaze may be exchanged between a patient and a medical staff. Therethrough, gaze may be exchanged between a patient and a medical staff without being covered by an interface window. Through the gaze exchange region, a medical staff may continuously observe parts, such as an upper body, a face, and eyes of a patient as well as mutual communion. In addition, according to the present invention, a window may be dynamically redisposed according to time by periodically updating a gaze exchange region through gaze tracking.

Here, when rearranging the interface windows, only the interfaces C1, C5, and C6 that overlap the gaze exchange region may be moved to an outer periphery of the gaze exchange region, and all interface windows may be moved to the outer periphery as illustrated in (b) of FIG. 3. In the rearrangement process, a movement distance of each interface window may be constant or may not be constant. In the case of the latter, the movement distance may be set to be shorter as the movement distance corresponds to the interface window disposed outside the center of a screen.

In this way, in the embodiment of the present invention, positions of pupils of a patient may be tracked by a camera in real time through the transparent display to recognize a gaze intersection point, and based on this, a medical software interface window for providing information may be automatically moved to an outer periphery and redisposed, and through this, a gaze exchange space is obtained between a doctor and a patient and the doctor and the patient may check various charts while communing with each other.

In addition, in the embodiment of the present invention, positions of pupils of a medical staff and a patient detected by each of the gaze trackers 120 and 130 are updated every time period, and thereby, a gaze intersection point may be periodically updated, and a gaze exchange region may also be changed in real time in response to a change in position of the gaze intersection point. Accordingly, when a seating position or a head position of either a patient or a medical staff changes, positions of the pupils and a gaze intersection point change, and accordingly, positions of the interface windows on the screen may be dynamically rearranged.

According to the embodiment of the present invention, a patient's entry is detected when a patient enters a treatment room, a position and eyes of the patient seated in front of a transparent display and a position and eyes of a medical staff waiting in advance are tracked in real time to obtain a gaze exchange line, and based on this, the interface windows are moved and redisposed such that the two people on both sides may exchange gaze without obstruction, and accordingly, gaze exchange and information exchange between the patient and a doctor may be done at the same time.

To this end, a medical treatment system according to an embodiment of the present invention may further include a motion sensor installed in a treatment room to detect whether a patient enters. The motion sensor may be installed at an entrance of a treatment room and may operate by being additionally connected to the control unit 150 of FIG. 1. Various means capable of detecting motion may be used as the motion sensor.

Here, when a patient's entry is detected through the motion sensor, the control unit 150 switches operations of the first and second gaze trackers 120 and 130 from an inactive state to an active state to start tracking pupils of a medical staff and the patient. In this way, the first and second gaze trackers 120 and 130 may be switched to an active state when a patient enters to detect pupils of a user within an angle of view of a camera, acquire coordinates of the user, track gaze of the user, and so on, and may transmit the obtained information to the control unit 150 in real time.

Figure 4:
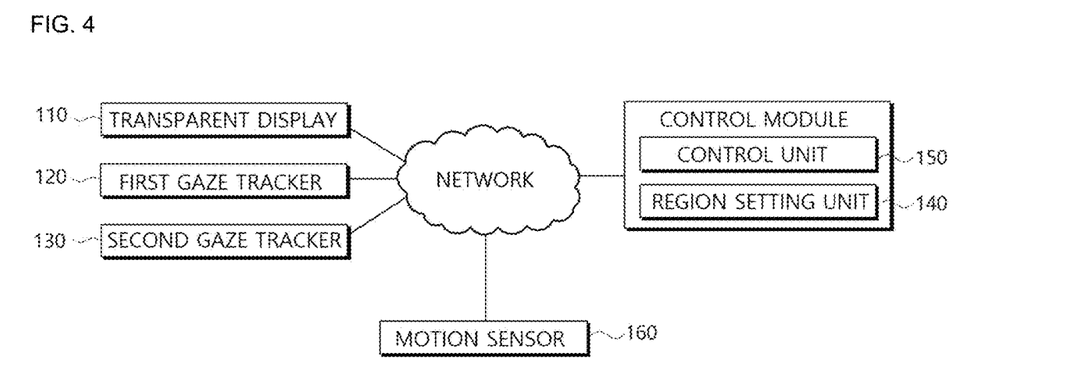
FIG. 4 is a diagram illustrating a modification example of the system illustrated in FIG. 1.

FIG. 4 is a diagram illustrating a modification example of the system illustrated in FIG. 1. A medical treatment system illustrated in FIG. 4 includes a transparent display 110, a first gaze tracker 120, a second gaze tracker 130, a region setting unit 140, a control unit 150, and a motion sensor 160, each of which is connected to each other through a network to exchange various data. Here, the network may include a wired network, a wireless network, or a mixture of the wired network and the wireless network. In addition, the control unit 150 and the region setting unit 140 may be modularized into a single control module and connected to the network.

In an embodiment of the present invention, the transparent display 110 may be implemented as a single-sided display or a double-sided display. When the transparent display 110 is implemented as a single-sided display, the control unit 150 displays a plurality of interface windows on one side of the transparent display 110 viewed by a medical staff in the form illustrated in FIGS. 2 and 3. In the single-sided type, the output information displayed on the side viewed by the medical staff may be implemented to be completely invisible from a patient in the back side, or may be implemented to be viewed partially dimly or to be transparent depending on transmission characteristics of the transparent display.

Figure 5:
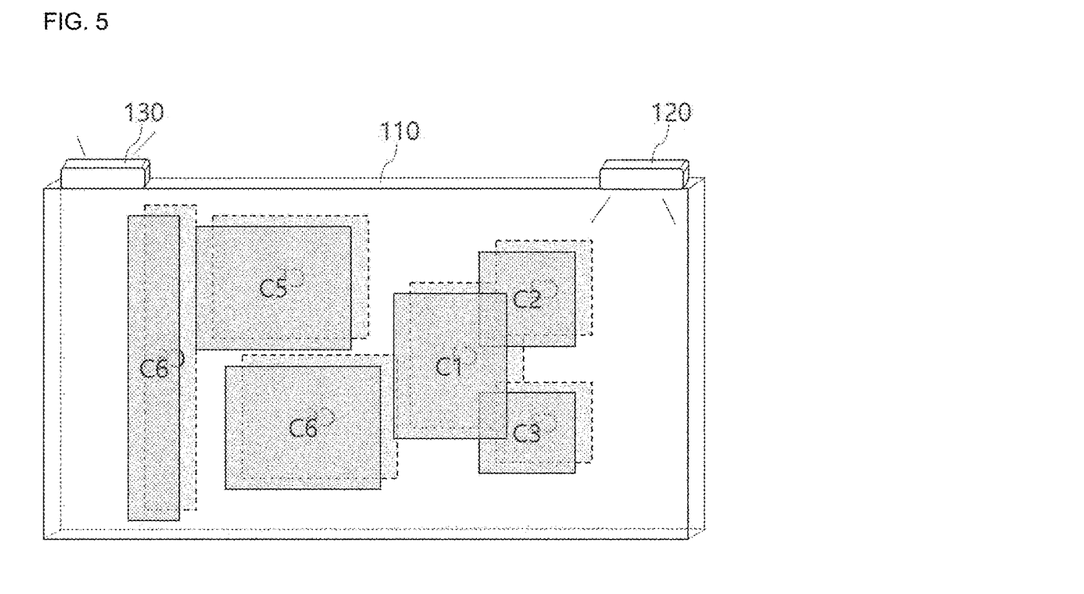
FIG. 5 is a view illustrating a double-sided transparent display according to an embodiment of the present invention.

FIG. 5 is a view illustrating a double-sided transparent display according to an embodiment of the present invention. As illustrated in FIG. 5, when the transparent display 110 is implemented as a double-sided display, the control unit 150 may display a plurality of interface windows corresponding to each other on both sides of the transparent display 110, and may display parallel to each other the respective interface windows on the same position on both sides. For example, a chart C1 is displayed side-by-side after the chart C1, and the chart C2 is displayed side-by-side after a chart C2. Here, although FIG. 5 illustrates that a screen of the back is reversed from a screen of the front in consideration of a user's point of view, the screen may be displayed as it is without reverse.

Figure 6:
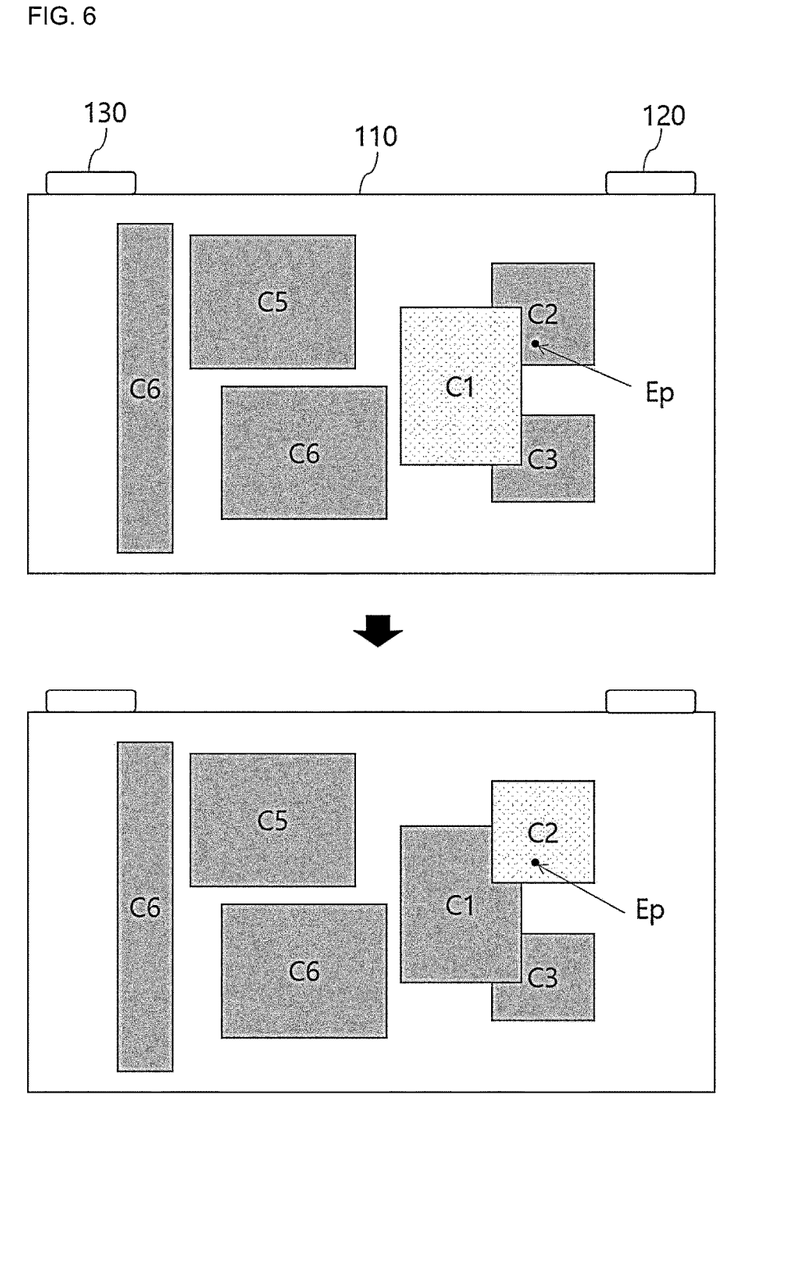
FIG. 6 is a view illustrating an interface window output method according to an embodiment of the present invention.

FIG. 6 illustrates an interface window output method according to an embodiment of the present invention. As illustrated in an upper portion of FIG. 6, the control unit 150 may arrange a plurality of interface windows in tiers on a screen of the transparent display 110, and the interface window with the highest priority may be displayed at a top portion based on a preset order or importance. In this case, the importance may be distinguished according to a time sequence or a chart type. For example, an MRI chart among a plurality of types of electronic medical treatment charts may be preferentially disposed at the top portion over other types. In addition, a clinician reviews a patient's past and current test results and inputs a prescription, which is related to the order of interviewing the patient, and windows with high importance may be preferentially disposed in each step.

In addition, when a screen gaze point Ep of a medical staff identified based on the gaze tracking information of the first gaze tracker 120 tracking the medical staff's gaze is maintained for a set time or more, the control unit 150 may move and dispose the target interface window C2 at a position corresponding to the screen gaze point Ep to the top portion as illustrated in a lower side. For example, when a medical staff's gaze stops at the screen gaze point Ep and maintains for more than 5 seconds, an interface window corresponding to a corresponding point may be disposed at the top portion of the screen. Of course, even when a medical staff directly touches the corresponding point, the same method may be applied in addition to the screen gaze.

In this case, when a double-sided display is used, the control unit 150 displays a plurality of interface windows corresponding to each other on both sides of a transparent display, but when the screen gaze point Ep of a medical staff is maintained for a set time as described above, the control unit 150 may simultaneously move all target interface windows corresponding to C2 on both sides of a position corresponding to the screen gaze point Ep to the top portion of the corresponding surface. Accordingly, the window C2 moves to the top of the screen that a patient looks at, and the patient may recognize a change of the screen to be induced to immediately look at the corresponding chart.

According to the present invention described above, gaze exchange and information transfer between a doctor and a patient are simultaneously performed based on a transparent display, and accordingly, patient satisfaction and treatment efficiency may be increased, the quality of medical care may be increased, and the spread of droplets in an epidemic situation may be prevented.

In addition, according to the present invention, a gaze intersection point between a patient and a doctor facing a transparent display is recognized, and based on this, medical software interfaces existing on a screen of the transparent display are automatically redisposed to an outer periphery therefrom, and accordingly, there are effects that charts may be checked without obstruction of gaze between the doctor and patient, and gaze exchange and interaction between the doctor and patient may be continued during treatment.

Although the present invention is described with reference to the embodiments illustrated in the drawings, this is merely an example, and those skilled in the art to which the present invention belongs will understand that various modifications and equivalent other embodiments may be made therefrom. Therefore, the true technical scope of protection of the present invention should be determined by the technical idea of the appended claims.

The invention claimed is:

1. A medical treatment system using a transparent display module, the medical treatment system comprising:
   a transparent display located between a patient and a medical staff and configured to display, on a screen, a plurality of interface windows for providing a plurality of electronic medical charts related to the patient;
   first and second gaze trackers respectively mounted on both sides of the transparent display to detect pupils of the medical staff and patient and provide gaze tracking information and configured to acquire positional coordinates of the pupils of the medical staff and patient in a three-dimensional space;
   a region setting unit configured to set a gaze exchange region based on an intersection point where a virtual connection line between the positional coordinates of the pupils of the medical staff and patient intersects a plane of the transparent display; and
   a control unit configured to rearrange the plurality of interface windows by moving at least one interface window overlapping the gaze exchange region outside the gaze exchange region.

2. The medical treatment system of claim 1, wherein
   the transparent display is implemented as a single-sided display, and
   the control unit displays the plurality of interface windows on one side of the transparent display viewed by the medical staff.

3. The medical treatment system of claim 1, wherein
   the transparent display is implemented as a double-sided display, and
   the control unit displays the plurality of interface windows on both sides of the transparent display so as to correspond to each other and displays the plurality of interface windows in parallel on the same position on the both sides.

4. The medical treatment system of claim 1, wherein
   the region setting unit sets a region of a set radius based on the intersection point or a region of a preset size and shape around the intersection point as the gaze exchange region.

5. The medical treatment system of claim 1, wherein
   the control unit arranges the plurality of interface windows on the screen of the transparent display in tiers so as to overlap each other and displays an interface window with a highest priority at a top portion based on a preset order or importance.

6. The medical treatment system of claim 5, wherein,
   when a screen gaze point of the medical staff identified based on gaze tracking information of the first gaze tracker for tracking gaze of the medical staff is maintained for a set time or more, the control unit moves a target interface window at a position corresponding to the screen gaze point to the top portion.

7. The medical treatment system of claim 6, wherein
   the control unit displays the plurality of interface windows on the both sides of the transparent display so as to correspond to each other, and when the screen gaze point is maintained for the set time, the control unit simultaneously moves all target interface windows on both sides of a position corresponding to the screen gaze point to a top portion of a corresponding surface.

8. The medical treatment system of claim 1, further comprising:

a motion sensor configured to detect entry of the patient into a treatment room, wherein, when the entry of the patient is detected through the motion sensor, the control unit switches operations of the first and second gaze trackers to an active state to start an operation of tracking the pupils of the medical staff and patient.

\* \* \* \* \*